US006207155B1

(12) United States Patent
Grimaldi et al.

(10) Patent No.: US 6,207,155 B1
(45) Date of Patent: Mar. 27, 2001

(54) METHOD OF EOSINOPHIL DEPLETION WITH ANTIBODY TO CCR 3 RECEPTOR

(75) Inventors: J. Christopher Grimaldi, San Francisco; Maureen C. Howard, Los Altos Hills; Robert L. Coffman, Portola Valley, all of CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/073,599

(22) Filed: May 6, 1998

Related U.S. Application Data

(60) Provisional application No. 60/045,806, filed on May 7, 1997.

(51) Int. Cl.$^7$ .......................... A61K 39/395; A61K 38/17
(52) U.S. Cl. ..................... 424/143.1; 424/130.1; 424/141.1; 514/2; 514/8; 514/12; 514/885
(58) Field of Search ............................ 514/2, 8, 12, 885; 424/130.1, 141.1, 143.1

(56) References Cited

U.S. PATENT DOCUMENTS 5,096,704    3/1992  Coffman, et al. .................... 424/85.8

FOREIGN PATENT DOCUMENTS

WO 97/41154    11/1997  (WO) .

OTHER PUBLICATIONS

Bonne et al. (1990) Science vol. 247, pp. 1306–1310.*
*Derwent World Patent Index*, Accession No. 97–226168, citing priority documents JP 96 41965, dated Feb. 28,1996; JP95–259067, dated Oct.5,1995, and WO 9712914 A, dated May16, 1997, with abstract.
Anne Burke–Gaffney, et al., *Biochem Biophys Res Commun*, 227:35–40, 1996. "Eotaxin Stimulates Eosinophil Adhesion to Human Lung Microvascular Endothelial Cells".
Robert L. Coffman, et al., *Science*, 245:308–310. Jul 21, 1989. "Antibody to Interleukin–5 Inhibits Helminith–Induced Eosinophilia in Mice".

Pierre Desreumaux, et al., *Current Opinion in Immunology*, 8:790–795, 1996. "Eosinophils in allergic reactions".
Eduardo A. Garcis–Zepeda, et al., *Journal of Immunology*, 157:5613–5626, 1996. "Human Monocyte Chemoattractant Protein (MCP)–4 Is a Novel CC Chemokine with Activities on Monocytes, Eosinophils, and Basophils Induced in Allergic and Nonallergic Inflammation That Signals Through the CC Chemokine Receptors (CCR)–2 and –3$^1$ ".
Jose–Angel Gonzalo, et al., *Journal of Clinical Investigation*, 98(10):2332–2345, Nov. 1996. "Eosinophil Recruitment to the Lung in a Murine Model of Allergic Inflammation The Role of T Cells, Chemokines, and Adhesion Receptors".
Heidi Heath, et al., *Journal of Clinical Investigation*, 99(2):178–184, Jan. 1997. "Chemokine Receptor Usage by Human Eosinophils The Importance of CCR3 Demonstrated Using an Antagonistic Monoclonal Antibody".
Hirohito Kita, et al., *Journal of Experimental Medicine*, 183:2421–2426, Jun. 1996. "Chemokines Active on Eosinophils: Potential Roles in Allegic Inflammation".
Paul D. Ponath, et al., *Journal of Experimental Medicine*, 183:2437–2448, Jun. 1996. "Molecular Cloning and Characterization of a Human Eotaxin Receptor Expressed Selectively on Eosinophils".
Marc E. Rothenberg, AAAAI/AAI/CIS Joint Major Symposium, San Francisco, CA. Feb. 24, 1997. "Chemokines and Their Receptors".
Robert I. Tepper, et al., *Science*, 257:548–551, Jul. 24, 1992. "An Eosinophil–Dependent Mechanism for the Antitumor Effect of Interleukin–4".

* cited by examiner

*Primary Examiner*—Prema Mertz
(74) *Attorney, Agent, or Firm*—Hugh Wang; Edwin P. Ching; Sheela Mohan-Peterson

(57) ABSTRACT

Binding compositions and various methods of use of the binding compositions are provided. In particular, a method is provided which comprises administering an effective amount of the binding composition, alone or in combination with other compounds, to eosinophils, thereby reducing the level of eosinophils in an individual. Preferably, the binding composition is a monoclonal antibody specific for CCR3.

10 Claims, No Drawings

METHOD OF EOSINOPHIL DEPLETION WITH ANTIBODY TO CCR 3 RECEPTOR

This application is a conversion of U.S. Provisional Patent Application U.S. Ser. No. 60/045,806, filed May 7, 1997, which is incorporated herein by reference, to a U.S. Utility Patent Application.

FIELD OF THE INVENTION

The invention relates generally to methods of depleting eosinophil levels and compositions used for such, and more particularly, to methods of treating diseases or conditions associated with elevated populations of eosinophils.

BACKGROUND

Eosinophils are white blood cells of the granulocytic lineage. Their normal functions include combating parasitic infections, particularly helminthic infections. See, e.g., Janeway, et al. (eds. 1996) *Immunobiology: The Immune System in Health and Disease* 2nd Ed., Garland Publishing, New York, N.Y.; and Rich (ed. 1996) *Clinical Immunology: Principles and Practice* Mosby, St. Louis, Mo. However, their accumulation in tissues, a condition referred to as eosinophilia, is also associated with several abnormal or disease states, including hypereosinophilia, chronic pneumonia, allergic bronchopulmonary aspergillosis, Churg-Strauss Syndrome, atopic dermatitis, and most notably asthma. See, e.g., Frigas, et al. (1986) *J. Allergy Clin. Immunol.* 77:527–537; Weller (1984) *J. Allergy Clin. Immunol.* 73:1–10; and Frank, et al. (eds. 1995) *Samter's Immunological Diseases* 5th Ed., vol. I–II, Little, Brown, and Co., Boston, Mass.

Currently glucocorticoid steroids are the preferred therapeutic drugs for treating the acute effects of allergic diseases, such as asthma. However, prolonged steroid treatment is associated with many deleterious side effects. See, e.g., Goodman and Gilman (eds.) *The Pharmacological Basis of Therapeutics* MacMillan Publishing Company, New York, N.Y. Moreover, the steroids apparently do not affect the production or accumulation of granulocytic cells, such as eosinophils, in the afflicted tissues. Such leads to treatment of symptoms rather than the underlying cause.

More recently, it has been shown that eosinophilia associated with certain immune disorders could be treated by the administration of an antagonist to interleukin-5 (IL-5). See, e.g., Coffman, et al. (1989) *Science* 245:308–310; and Coffman, et al. U.S. Pat. No. 5,096,704. IL-5 is a potent eosinophil differentiation factor, but also exerts effects on other immune cells, e.g., B cells. However, this antagonist can affect other cell types besides eosinophils.

The availability of alternative or complementary approaches to the treatment of disorders associated with eosinophilia would have important clinical utility. Preventing the production or accumulation of eosinophils in the relevant tissues may block the underlying cause of these disorders or diseases.

SUMMARY OF THE INVENTION

The invention provides a method of depleting eosinophils by administering an effective amount of an antagonist against the receptor for an eosinophil chemokine, eotaxin. Applicants have observed that this leads to a decrease in the number of eosinophils. The receptor, designated CCR3 is expressed predominantly on eosinophils. Preferably, the antagonists to CCR3 are monoclonal antibodies, or binding compositions derived therefrom by standard techniques.

The present invention provides an antibody or binding composition which specifically binds a CCR3 receptor, reduces the level of eosinophilia in a sample, and does not block ligand binding. In preferred embodiments the antibody is a monoclonal antibody. Also provided is a sterile composition comprising the antibody or binding composition and a pharmaceutically acceptable carrier.

The invention encompasses a method of ameliorating an eosinophil related disease or disorder in an individual by administering an effective amount of the antibody or binding composition, either alone or in combination with an antagonist to interleukin-5 (IL-5) or a steroid. In preferred embodiments the antibody is a monoclonal antibody. An effective amount of the antibody or binding composition is, e.g., preferably at least 500 µg/kg body weight; usually at least 1000 µg/kg body weight; typically at least 5 mg/kg body weight; or ordinarily at least 10 mg/kg body weight; and ordinarily less than 100 mg/kg body weight; typically less than 50 mg/kg body weight; or usually less than 25 mg/kg body weight per week. Amelioration is a reduction in the level of eosinophils, e.g., 10%, 20%, 30%, or 50% or more. The eosinophil related disease may be a pulmonary inflammation; a dermatitis; or a hypereosinophilia. The antagonist to IL-5 can be an intact monoclonal antibody, a binding fragment thereof, a soluble receptor for IL-5, or an IL-5 mutein.

An effective amount of an IL-5 monoclonal antibody, binding fragment thereof, or soluble receptor is preferably at least 1 µg/kg body weight; usually at least 5 µg/kg body weight; or typically at least 10 µg/kg body weight; and generally less than 1000 µg/kg body weight; usually less than 500 µg/kg body weight; or preferably less than 100 µg/kg body weight per week. An effective amount of the mutein is preferably at least 100 µg/hour; usually at least 500 µg/hour; typically at least 1 mg/hour; and ordinarily at least 3 mg/hour; and preferably less than 100 mg/hour; usually less than 30 mg/hour; typically less than 10 mg/hour; or ordinarily less than 6 mg/hour. An effective amount or the steroid is preferably at least 1 mg/day; usually at least 2 mg/day; or typically at least 5 mg/day; and is ordinarily less than 100 mg/day; typically less than 50 mg/day; usually less than 20 mg/day; or preferably less than 10 mg/day.

The present invention further provides a method for detecting for the presence of eosinophils in a sample comprising the steps of contacting the sample with the antibody or binding composition and detecting the binding of the antibody or binding composition to a CCR3 receptor on the eosinophils. In preferred embodiments, the antibody is a monoclonal antibody and the antibody is detectably labeled.

Also encompassed is a method of isolating a population of cells expressing the CCR3 receptor from a mixture of cells by contacting the mixture with the antibody or binding composition and isolating the population of cells. In preferred embodiments the antibody is a monoclonal antibody. The antibody or binding composition is detectably labeled with a fluorescent moiety, a radioactive moiety, or is coupled to a magnetic bead. The cells are isolated by Fluorescent Activated Cell Sorting (FACS), or by magnetic cell sorting.

DETAILED DESCRIPTION OF THE INVENTION

Outline

I. General

II. Making antibodies

A. Making antigen

B. Making antibodies; binding compositions

C. Selecting mAb isotypes; binding composition conjugates

III. Immunoassays
IV. Uses

I. General

The invention is based, in part, on the discovery that a receptor for an eosinophil specific chemokine, eotaxin, is expressed predominantly on eosinophils. From an entire panel of about 30 monoclonal antibodies (mAb) surprisingly two mAbs were able to significantly reduce the level of eosinophils in mice parasitized with a helminth but without blocking ligand binding to the receptor. The reduced levels may be attributable to any of several mechanisms, e.g., complement fixation/depletion or opsonization by macrophages. See, e.g., Janeway, et al. (eds. 1996) *Immunobiology* Garland Publishing Inc., New York, N.Y.

The chemokines are a sub-family of chemoattractant cytokines that classically mediate leukocyte trafficking by binding to specific G-protein linked seven transmembrane spanning receptors. Chemokines are divided into four groups based on the primary sequence of the first two cysteines: the CXC, CC, C, and the newly discovered, CX3C families. The CXC and C chemokine families are effective predominantly on neutrophils and lymphocytes, respectively. The CC chemokines are preferentially effective on macrophages, lymphocytes, and eosinophils. Eosinophil specific chemokines include, e.g., RANTES, MCP-2, MCP-3, MCP-4, MIP-1α, and recently described, eotaxin. See, e.g., Alam, et al. (1993) *J. Immunol.* 150:3442–3448; Weber, et al. (1995) *J. Immunol.* 154:4166–4172; Dahinden, et al. (1994) *J. Exp. Med.* 179:751–756; Uguccioni, et al. (1996) *J. Exp. Med.* 183:2379–2384; Rot, et al. (1992) *J. Exp. Med.* 176:1489–1495; and Garcia-Zepeda, et al. (1996) *J. Immunol.* 157:5613–5626.

II. Making Antibodies; Binding Compositions

The present invention provides for the use of an antibody or binding composition which specifically binds to a CCR3, preferably mammalian, e.g., primate, human, cat, dog, rat, or mouse. Antibodies can be raised to various CCR3 proteins, including individual, polymorphic, allelic, strain, or species variants, and fragments thereof, both in their naturally occurring (full-length) forms or in their recombinant forms. Particularly interesting epitopes include those accessible from the extracellular space. Additionally, antibodies can be raised to CCR3 proteins in both their native (or active) forms or in their inactive, e.g., denatured, forms. Anti-idiotypic antibodies may also be used.

A number of immunogens may be selected to produce antibodies specifically reactive with CCR3 proteins, e.g., as expressed on cells. Recombinant protein is a preferred immunogen for the production of monoclonal or polyclonal antibodies. Naturally occurring protein, from appropriate sources, e.g., primate, rodent, etc., may also be used either in pure or impure form. See, e.g., GenBank and NCBI databases. Synthetic peptides, made using, e.g., the human CCR3 protein sequences described herein, may also be used as an immunogen for the production of antibodies to CCR3 proteins. Recombinant protein can be expressed and purified in eukaryotic or prokaryotic cells as described, e.g., in Coligan, et al. (eds. 1995 and periodic supplements) *Current Protocols in Protein Science* John Wiley & Sons, New York, N.Y.; and Ausubel, et al (eds. 1987 and periodic supplements) *Current Protocols in Molecular Biology* Greene/Wiley, New York, N.Y. Naturally folded or denatured material can be used, as appropriate, for producing antibodies. Either monoclonal or polyclonal antibodies may be generated, e.g., for subsequent use in immunoassays to measure the protein, or for immunopurification methods.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the CCR3 protein of interest. For example, when appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane; or Coligan. Isotype classes may be selected, or antagonists with specific desired properties, e.g., not blocking ligand binding. Immunization can also be performed through other methods, e.g., DNA vector immunization. See, e.g., Wang, et al. (1997) *Virology* 228:278–284.

Monoclonal antibodies may be obtained by various techniques familiar to those skilled in the art. Typically, spleen cells from an animal immunized with a desired antigen are immortalized, commonly by fusion with a myeloma cell. See, Kohler and Milstein (1976) *Eur. J. Immunol.* 6:511–519. Alternative methods of immortalization include transformation with Epstein Barr Virus, oncogenes, or retroviruses, or other methods known in the art. See, e.g., Doyle, et al. (eds. 1994 and periodic supplements) *Cell and Tissue Culture: Laboratory Procedures* John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies or binding compositions, including binding fragments and single chain versions, against predetermined fragments of CCR3 proteins can be raised by immunization of animals with conjugates of the fragments with carrier proteins as described above. Monoclonal antibodies are prepared from cells secreting the desired antibody. These antibodies can be screened for binding to normal or defective CCR3 protein, or screened for eosinophil depleting ability. These monoclonal antibodies will usually bind with at least a KD of about 1 mM, more usually at least about 300 μM, typically at least about 10 μM, more typically at least about 30 μM, preferably at least about 10 μM, and more preferably at least about 3 μM or better.

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma"

that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) *Proc. Nat'l Acad. Sci. USA* 86:10029–10033; or made in transgenic mice, see Mendez, et al. (1997) *Nature Genetics* 15:146–156.

Antibodies are merely one form of specific binding compositions. Other binding compositions, which will often have similar uses, include molecules that bind with specificity to CCR3 receptor, e.g., in a binding partner-binding partner fashion, an antibody-antigen interaction, or in a natural physiologically relevant protein-protein interaction, either covalent or non-covalent, e.g., proteins which specifically associate with CCR3 receptor protein. The molecule may be a polymer, or chemical reagent. A functional analog may be a protein with structural modifications, or may be a structurally unrelated molecule, e.g., which has a molecular shape which interacts with the appropriate binding determinants.

Antibody binding compounds, including binding fragments, of this invention can have significant diagnostic or therapeutic value. They can be useful as non-neutralizing binding compounds and can be coupled to toxins or radionuclides so that when the binding compound binds to the antigen, a cell expressing it, e.g., on its surface, is killed. Further, these binding compounds can be conjugated to drugs or other therapeutic agents, either directly or indirectly by means of a linker, and may effect drug targeting.

III. Immunoassays

Immunoassays are valuable in diagnosing a disease or disorder associated with eosinophilia, or monitoring the level of depletion of eosinophils in a treated patient. A particular protein can be measured by a variety of immunoassay methods. For a review of immunological and immunoassay procedures in general, see, e.g., Stites and Terr (eds. 1991) *Basic and Clinical Immunology* (7th ed.). Moreover, the immunoassays of the present invention can be performed in many configurations, which are reviewed extensively, e.g., in Maggio (ed. 1980) *Enzyme Immunoassay* CRC Press, Boca Raton, Fla.; Tijan (1985) "Practice and Theory of Enzyme Immunoassays," *Laboratory Techniques in Biochemistry and Molecular Biology* Elsevier Science Publishers B. V., Amsterdam; and Harlow and Lane *Antibodies, A Laboratory Manual*, supra. See also Chan (ed. 1987) *Immunoassay: A Practical Guide* Academic Press, Orlando, Fla.; Price and Newman (eds. 1991) *Principles and Practice of Immunoassays* Stockton Press, New York; and Ngo (ed. 1988) *Non-isotopic Immunoassays* Plenum Press, New York.

Immunoassays for measurement of CCR3 proteins or peptides can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with CCR3 proteins produced as described above. The concentration of labeled analyte bound to the capture agent is inversely proportional to the amount of free analyte present in the sample.

In a competitive binding immunoassay, the CCR3 protein present in the sample competes with labeled protein for binding to a specific binding agent, for example, an antibody specifically reactive with the CCR3 protein. The binding agent may be bound to a solid surface to effect separation of bound labeled protein from the unbound labeled protein. Alternately, the competitive binding assay may be conducted in liquid phase and a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

CCR3 proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of CCR3 proteins in a sample. Electrophoresis is carried out, e.g., on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above may employ labeled assay components. The label may be coupled directly or indirectly to the desired component of the assay according to methods well known in the art. A wide variety of labels and methods may be used. Traditionally, a radioactive label incorporating $^3$H, $^{125}$I, $^{35}$S, $^{14}$C, or $^{32}$P was used.

Non-radioactive labels include entities which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which may be used, see U.S. Pat. No. 4,391,904.

Antibodies reactive with a particular protein can also be measured by a variety of immunoassay methods. Thus modifications of the above procedures may be used to determine the amounts or affinities of various CCR3 antibodies or antibody preparation. For a review of immunological and immunoassay procedures applicable to the measurement of antibodies by immunoassay techniques, see, e.g., Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

Screens to evaluate the binding and activity of mAbs and binding compositions encompass a variety of methods. Binding can be assayed by detectably labeling the antibody or binding composition as described above. Cells expressing a CCR3 receptor are incubated with this antibody or binding composition, and binding is assayed by Fluorescence Activated Cell Sorting (FACS) analysis.

To evaluate eosinophil depletion ability, experimental animals, e.g., mice, are preferably induced into eosinophilia, e.g., by infection with a parasite. Eosinophil counts are made prior to and at various time points after administration of a bolus of the candidate mAb or binding composition. Levels are analyzed in various samples, e.g., blood, serum, nasal or pulmonary lavages, or tissue biopsy staining. A successful mAb or binding composition will significantly lower the level of circulating eosinophils.

Evaluation of antibodies can be performed in other animals, e.g., humans using various methods. For example, blood samples are withdrawn from patients suffering from an eosinophil related disease or disorder before and after treatment with a candidate mAb and eosinophil counts are taken. The antibodies can be used in a diagnostic context to evaluate the extent of eosinophilia, e.g., by FACS, tissue staining, in vitro culture.

IV. Uses

The present invention is useful in the treatment of diseases associated with eosinophilia, e.g., pulmonary inflammation, dermatitis, etc. See, e.g., Hardy, et al. (1968) *Ann. Intern. Med.* 68:1220–1229. Pulmonary inflammation includes, e.g., asthma, chronic pneumonia, allergic rhinitis, allergic bronchopulmonary aspergillosis, hypereosinophilia, or Churg-Strauss syndrome. See, e.g., Frank, et al. (eds. 1995) *Samter's Immunologic Diseases* 5th Ed., vols. I–II, Little, Brown and Co., Boston, Mass.; Coffman, et al (1989) *Science* 245:308–310; and Frick, et al. (1988) *J. Allergy Clin. Immunol.* 82:199–225. Dermatological diseases include, e.g., atopic dermatitis, see, e.g., Uehara, et al. (1990) *Clin. Exp. Dermatol.* 15:264–266. The present invention can be administered alone or in combination with another inhibitor of eosinophilia, e.g., interleukin-5 (IL-5) antagonists; or other compounds used for the treatment of symptoms, e.g., steroids such as glucocorticoids.

To prepare pharmaceutical or sterile compositions including the CCR3 antibody or binding composition thereof, the antibody or binding composition is admixed with a pharmaceutically acceptable carrier or excipient which is preferably inert. Preparation of such pharmaceutical compositions is known in the art, see, e.g., *Remington's Pharmaceutical Sciences* and *U.S. Pharmacopeia: National Formulary* Mack Publishing Company, Easton, Pa. (1984).

Antibodies or binding compositions are normally administered parenterally, preferably intravenously. Since such protein or peptide antagonists may be immunogenic they are preferably administered slowly, either by a conventional IV administration set or from a subcutaneous depot, e.g. as taught by Tomasi, et al., U.S. Pat. No. 4,732,863.

When administered parenterally the antibodies or fragments will be formulated in a unit dosage injectable form (solution, suspension, emulsion) in association with a pharmaceutically acceptable parenteral vehicle. Such vehicles are preferably inherently nontoxic and nontherapeutic. The antagonist may be administered in aqueous vehicles such as water, saline, or buffered vehicles with or without various additives and/or diluting agents. Alternatively, a suspension, such as a zinc suspension, can be prepared to include the peptide. Such a suspension can be useful for subcutaneous (SQ) or intramuscular (IM) injection. The proportion of antagonist and additive can be varied over a broad range so both are present, or the combination is, in effective amounts. The antibody is preferably formulated in purified form substantially free of aggregates, other proteins, endotoxins, and the like, at concentrations of, e.g., about 5 to 30 mg/ml, preferably 10 to 20 mg/ml. Preferably, the endotoxin levels are less than 2.5 EU/ml. See, e.g., Avis, et al. (eds. 1993) *Pharmaceutical Dosage Forms: Parenteral Medications* 2d ed., Dekker, N.Y.; Lieberman, et al. (eds. 1990) *Pharmaceutical Dosage Forms: Tablets* 2d ed., Dekker, N.Y.; Lieberman, et al. (eds. 1990) *Pharmaceutical Dosage Forms: Disperse Systems* Dekker, N.Y.; Fodor, et al. (1991) *Science* 251:767–773, Coligan (ed.) *Current Protocols in Immunology;* Hood, et al. *Immunology* Benjamin/Cummings; Paul (ed.) *Fundamental Immunology* Academic Press; Parce, et al. (1989) *Science* 246:243–247; Owicki, et al. (1990) *Proc. Nat'l Acad. Sci. USA* 87:4007–4011; and Blundell and Johnson (1976) *Protein Crystallography* Academic Press, New York.

Selecting an administration regimen for an antagonist depends on several factors, including the serum or tissue turnover rate of the antagonist, the level of eosinophilia, the immunogenicity of the antagonist, the accessibility of the target eosinophils (e.g., if non-serum eosinophils are to be blocked). Preferably, an administration regimen maximizes the amount of antagonist delivered to the patient consistent with an acceptable level of side effects. Accordingly, the amount of antagonist delivered depends in part on the particular antagonist and the severity of the condition being treated. Guidance in selecting appropriate doses is found in the literature on therapeutic uses of antibodies, e.g. Bach et al., chapter 22, in Ferrone, et al., (eds. 1985) *Handbook of Monoclonal Antibodies* Noges Publications, Park Ridge, N.J.; and Russell, pp. 303–357, and Smith et al., pp. 365–389, in Haber, et al. (eds. 1977) *Antibodies in Human Diagnosis and Therapy* Raven Press, New York, N.Y.

Determination of the appropriate dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. Circulating eosinophil levels would be important indicators of when an effective dose is reached, along with measures of symptoms of the inflammation, e.g., level of inflammatory cytokines produced. Preferably, a CCR3 antibody or binding composition thereof that will be used is derived from the same species as the animal targeted for treatment, thereby minimizing a humoral response to the reagent.

The total weekly dose ranges for antibodies or fragments thereof, which specifically bind to CCR3 range generally from about 10 μg, more generally from about 100 μg, typically from about 500 μg, more typically from about 1000 μg, preferably from about 5 mg, and more preferably from about 10 mg per kilogram body weight. Generally the range will be less than 100 mg, preferably less than about 50 mg, and more preferably less than about 25 mg per kilogram body weight.

The weekly dose ranges for antagonists of IL-5 activity, e.g., antibody, binding fragments, or soluble receptors, range from about 1 μg, preferably at least about 5 μg, and more preferably at least about 10 μg per kilogram of body weight. Generally, the range will be less than about 1000 μg, preferably less than about 500 μg, and more preferably less than about 100 μg per kilogram of body weight. Dosages are on a schedule which effects the desired treatment and can be periodic over shorter or longer term. In general, ranges will be from at least about 10 μg to about 50 mg, preferably about 100 μg to about 10 mg per kilogram body weight.

Other antagonists of IL-5 activity, e.g., muteins, are also contemplated. Hourly dose ranges for IL-5 muteins range from at least about 100 μg, generally at least about 500 μg, typically at least about 1 mg, and preferably at least 3 mg per hour. Generally the dosage will be less than about 100 mg, typically less than about 30 mg, preferably less than about 10 mg, and more preferably less than about 6 mg per hour. General ranges will be from at least about 1 μg to about 1000 μg, preferably about 10 μg to about 500 μg per hour.

The present invention also provides for administration of CCR3 antibodies or binding compositions in combination with known therapies, e.g., steroids, particularly glucocorticoids, which alleviate the symptoms associated with eosinophilia. Daily dosages for glucocorticoids will range from at least about 1 mg, generally at least about 2 mg, and preferably at least about 5 mg per day. Generally, the dosage will be less than about 100 mg, typically less than about 50 mg, preferably less than about 20 mg, and more preferably less than about 10 mg per day. In general, the ranges will be from at least about 1 mg to about 100 mg, preferably from about 2 mg to 50 mg per day.

The phrase "effective amount" means an amount sufficient to ameliorate a symptom or sign of the inflammatory condition. Typical mammalian hosts will include mice, rats, cats, dogs, and primates, including humans. An effective amount for a particular patient may vary depending on factors such as the condition being treated, the overall health of the patient, the method route and dose of administration and the severity of side affects. When in combination, an effective amount is in ratio to a combination of components and the effect is not limited to individual components alone.

An effective amount of antagonist will decrease the symptoms typically by at least about 10%; usually by at least about 20%; preferably at least about 30%; or more preferably at least about 50%. The present invention provides reagents which will find use in therapeutic applications as described elsewhere herein, e.g., in the general description for treating disorders associated with eosinophilia. See, e.g., Berkow (ed.). *The Merck Manual of Diagnosis and Therapy* Merck & Co., Rahway, N.J.; Thorn, et al. *Harrison's Principles of Internal Medicine* McGraw-Hill, New York; Gilman, et al. (eds. 1990) *Goodman and Gilman's: The Pharmacological Bases of Therapeutics* 8th Ed., Pergamon Press; *Remington's Pharmaceutical Sciences*, 17th ed. (1990), Mack Publishing Co., Easton, Pa.; Langer (1990) *Science* 249:1527–1533; and *Merck Index*, Merck & Co., Rahway, N.J.

Antibodies to CCR3 proteins may be used for the identification or sorting of cell populations expressing CCR3 protein, e.g., eosinophils. Methods to sort such populations are well known in the art, see, e.g., Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y. Populations of cells expressing the CCR3 receptor can also be purified using magnetic beads as described, e.g., in Bieva, et al. (1989) Exp. Hematol. 17:914–920; Hernebtub, et al. (1990) *Bioconj. Chem.* 1:411–418; Vaccaro, et al. (1990) *Am. Biotechnol. Lab.* April 1990.

Using the assay methods described above, the antibodies or binding compositions are useful in diagnosing diseases states which result in elevated eosinophil numbers. Labeled antibodies can also be utilized in analyzing eosinophil infiltration in tissues. Antibodies raised against each CCR3 protein will also be useful to raise anti-idiotypic antibodies. These will be useful in detecting or diagnosing various immunological conditions related to expression of the respective antigens.

The broad scope of this invention is best understood with reference to the following examples, which are not intended to limit the inventions to the specific embodiments.

EXAMPLES

I. General Methods

Some standard methods of molecular biology are described or referenced, e.g., in Maniatis, et al. (1982) *Molecular Cloning: A Laboratory Manual* Cold Spring Harbor Laboratory, Cold Spring Harbor Press; Sambrook, et al. (1989) *Molecular Cloning: A Laboratory Manual* (2d ed.), vols. 1–3, CSH Press, New York; Ausubel, et al., *Biology* Greene Publishing Associates, Brooklyn, N.Y.; Ausubel, et al. (1987 and Supplements) Current Protocols in Molecular Biology Greene/Wiley, New York; or Innis, et al. (eds. 1990) *PCR Protocols: A Guide to Methods and Applications* Academic Press, New York Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; manufacturer's literature on use of protein purification products, e.g., Pharmacia, Piscataway, N.J., or Bio-Rad, Richmond, Calif.; and Coligan, et al. (eds. 1995 and periodic supplements) Current Protocols in Protein Science, John Wiley & Sons, New York, N.Y. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, New York; and Crowe, et al. (1992) QIAexpress: The High Level Expression & Protein Purification System QIAGEN, Inc., Chatsworth, Calif.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Production Cell Lines Expressing CCR3

Mammalian cells, e.g., NIH3T3, were transfected by electroporation or lipofectamine (Gibco BRL, Gaithersburg, Md.) and selected in neomycin supplemented media for two weeks. Resistant colonies were sorted by FACS into 96 well plates and allowed to proliferate. RNA was isolated from individual clones using RNAzol (Friendswood, Tex.) and analyzed using RTPCR see, e.g., Ausubel, et al. (1987 and Supplements) *Current Protocols in Molecular Biology* Greene/Wiley, New York; Innis, et al. (eds. 1990) *PCR Protocols: A Guide to Methods and Applications* Academic Press, New York, following treatment with DNase.

Positive clones were subject to further analysis in a Ca++ flux assay as described, e.g., in Kelner, et al. (1994) *Science* 266:1395–1399, using eotaxin as the ligand for CCR3. The clone exhibiting the highest Ca++ flux was expanded for use in generating mAbs.

Other methods of evaluation of expression can also be utilized, e.g., staining and FACS analysis, tissue staining, northern analysis, etc.

III. Monoclonal Antibodies

Lewis rats were immunized with 108 Y3/CCR3 transfected cells intraperitoneally every 2 weeks for 8 weeks. The final immunization was given intravenously (IV) through the tail vein. Four days after the IV injection, the spleen was removed and fused to SP2/0 and NS1 cells. HAT resistant hybridomas were selected using a protocol designed by Stem Cell Technologies (Vancouver, BC). After 10 days of HAT selection, resistant foci were transferred to 96 well plates and expanded for 3 days. Antibody containing supernatants were analyzed by FACS for binding to NIH3T3/CCR3 transfectants. 29 different CCR3 mAbs were produced.

Additionally, some of the mAbs were used to sort CCR3 positive cells in spleens from RAG −/− mice sensitized with *Aspergillus fumagatus*. The sorted cells all appeared to be eosinophils as determined by Wright Giemsa staining.

IV. Depletion of Circulating Eosinophils

All mAbs were isotyped as directed in an ELISA based kit from Zymed, Inc. (So. San Francisco, Calif.) and in an Ouchterlony based kit from ICN (Aurora, Ohio). The mAbs had isotypes of IgG2A, IgG2B, and IgG2C. Using two IgG2B mAbs, designated 6S2-19-4 and 6SH2-88, as well as an IgG2A mAb, designated 6SH2-59, eosinophil depletion assays were performed. Neither of these antibodies was able to block eotaxin binding to CCR3. Balb/C mice were injected subcutaneously with 500 Nippostrongylus brasiliensis larvae in order to induce eosinophilic pneumonia. 9 to 14 days post infection, a bolus of 0.5 mg of either 6S2-19-4 or 6SH2-59 was administered IP. Eosinophil counts were analyzed before and after administration of the mAbs by staining of blood drawn from the tail vein. 6SH2-59 did not significantly deplete circulating eosinophils, while 6S2-19-4 and 6SH2-88 significantly depleted these cells. Interestingly, the level of circulating eosinophils remained low for at least seven days. 6S2-19-4 was deposited with American Type Culture Collection (ATCC; 12301 Parklawn Drive, Rockville, Md.), on Apr. 30, 1997, ATCC No.HB12351.

Analysis of human antibodies can be evaluated in a similar manner. A biological sample, e.g., blood, tissue biopsy sample, lung or nasal lavage, skin punch, is obtained from an individual suffering from a disease or disorder associated with eosinophilia. Eosinophil counts are taken as described previously. A mAb, or binding composition, which specifically binds to the human CCR3 receptor is administered alone or in combination with another compound, e.g., an IL-5 antagonist or a steroid, to the individual. An effective treatment is measured by the amelioration of symptoms, e.g., alleviation of pulmonary or dermal inflammation, or by measuring eosinophil counts in biological samples at various time points.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of ameliorating an eosinophilia related disease or disorder in an individual comprising administering an effective amount of an antibody which specifically binds a CCR3 receptor; wherein said antibody is of the IgG2B isotype that reduces the level of eosinophils in said individual and does not block ligand binding to said receptor.

2. The method of claim 1, wherein said antibody is administered in an effective combination with:
   (a) an antagonist to interleukin-5 (IL-5); or
   (b) a steroid.

3. The method of claim 1, wherein said antibody is a monoclonal antibody.

4. The method of claim 1, wherein said effective amount of said antibody is:
   (a) at least 500 µg/kg body weight per week;
   (b) at least 1000 µg/kg body weight per week;
   (c) at least 5 mg/kg body weight per week;
   (d) at least 10 mg/kg body weight per week;
   (e) less than 100 mg/kg body weight per week;
   (f) less than 50 mg/kg body weight per week; or
   (g) less than 25 mg/kg body weight per week.

5. The method of claim 1, wherein said ameliorating is accompanied by a reduction of the level of eosinophils.

6. The method of claim 2, wherein said antagonist is:
   a) an intact monoclonal antibody;
   b) a binding fragment of said monoclonal antibody;
   c) a soluble receptor for IL-5; or
   d) an IL-5 mutein.

7. The method of claim 6, wherein said antagonist is said intact monoclonal antibody, said binding fragment thereof, or said soluble receptor; and the amount of said antagonist is:
   a) at least 1 µg/kg body weight per week;
   b) at least 5 µg/kg body weight per week;
   c) at least 10 µg/kg body weight per week;
   d) less than 1000 µg/kg body weight per week;
   e) less than 500 µg/kg body weight per week; or
   f) less than 100 µg/kg body weight per week.

8. The method of claim 6, wherein said antagonist is said mutein and the amount of said mutein is:
   (a) at least 100 µg/hour;
   (b) at least 500 µg/hour;
   (c) at least 1 mg/hour;
   (d) at least 3 mg/hour;
   (e) less than 100 mg/hour;
   (f) less than 30 mg/hour;
   (g) less than 10 mg/hour;
   (h) less than 6 mg/hour.

9. The method of claim 2, wherein said effective amount of said steroid is:
  a) at least 1 mg/day;
  b) at least 2 mg/day;
  c) at least 5 mg/day;
  d) less than 100 mg/day;
  e) less than 50 mg/day;
  f) less than 20 mg/day; or
  g) less than 10 mg/day.

10. The method of claim 1, wherein said eosinophilia related disease is:
  a) a pulmonary inflammation;
  b) a dermatitis; or
  c) a hypereosinophilia.

* * * * *